(12) United States Patent
Carman et al.

(10) Patent No.: US 6,509,500 B2
(45) Date of Patent: Jan. 21, 2003

(54) CONTINUOUS PREPARATION OF INCORPORATED PHOTOGRAPHIC AMIDES

(75) Inventors: Harold Evans Carman, Suwanee, GA (US); Eleanor Hawkins Cwirko, Kingsport, TN (US); Robert Joseph Maleski, Kingsport, TN (US); Karen Marie Richards, Portage, MI (US); Jerry Neal Schlather, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 09/865,134

(22) Filed: May 24, 2001

(65) Prior Publication Data
US 2002/0177731 A1 Nov. 28, 2002

(51) Int. Cl.⁷ .................... C07C 231/00; G03C 1/08; G03C 1/46
(52) U.S. Cl. ............. 564/142; 564/133; 564/143; 430/543; 430/503; 430/553
(58) Field of Search ................ 564/133, 142, 564/143; 430/543, 503, 553

(56) References Cited

U.S. PATENT DOCUMENTS

| 2,801,171 A | 7/1957 | Fierke et al. |
| 2,875,027 A | 2/1959 | McCrossen et al. |
| 3,062,653 A | 11/1962 | Weissberger et al. |
| 4,124,396 A | * 11/1978 | Osbon et al. |
| 5,009,989 A | 4/1991 | Aoki et al. |
| 5,041,605 A | 8/1991 | Huson et al. |
| 5,442,114 A | * 8/1995 | Takamine et al. |
| 5,561,037 A | 10/1996 | Jain et al. |

FOREIGN PATENT DOCUMENTS

EP    0608896 A1    8/1994

OTHER PUBLICATIONS

T. H. James, "The Theory of the Photographic Process", Fourth Edition, Eastman Kodak, 1977, pp. 339–353.

* cited by examiner

*Primary Examiner*—Jafar F. Parsa
(74) *Attorney, Agent, or Firm*—Michael J. Blake; Bernard J. Graves, Jr.

(57) ABSTRACT

This invention relates to a method of making an incorporated photographic amide comprising a) continuously combining an amine capable of forming an incorporated photographic amide, an acid chloride, one or more acid-absorbing reagents, and one or more water-immiscible solvents to continuously form a reaction mixture; b) continuously reacting the amine and acid chloride to form an incorporated photographic amide; and c) separating the incorporated photographic amide from the reaction mixture.

7 Claims, 5 Drawing Sheets

CONTINUOUS PREPARATION OF INCORPORATED PHOTOGRAPHIC AMIDES

FIELD OF THE INVENTION

The present invention relates to the preparation of incorporated photographic amides. More particularly, the present invention relates to the preparation of incorporated photographic amides using a continuous process.

BACKGROUND OF THE INVENTION

Amides are important functional groups in photographic couplers that are incorporated into photographic elements. Such couplers, known as incorporated photographic couplers, are highly water insoluble since they must not diffuse in the aqueous media used in the photographic element (T. H. James, Editor, "The Theory of the Photographic Process," Fourth Ed., Eastman Kodak, 1977, page 345).

Amides link the photographic dye-forming portion of the coupler to the parts of the molecule that control dye diffusion, hue, stability, and other photographically important properties. (T. H. James, supra). Amides also serve as important functional groups in incorporated photographic stabilizers that retard the degradation of the image dye that results from reaction of the photographic couplers with developing agents. See U.S. Pat. No. 5,561,037. Such amides are commonly known as, and are referred to in this application as, incorporated photographic amides.

In most cases, incorporated photographic amides are prepared by combining acid chlorides, or solutions of acid chlorides, and amines dissolved in organic solvent using a batch operation:

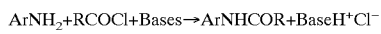

ArNH$_2$+RCOCl+Bases→ArNHCOR+BaseH$^+$Cl$^-$

In the batch process described in U.S. Pat. No. 2,801,171 to Fierke et al., water is excluded from the amide preparation process and an organic base such as pyridine is used to neutralize the acid released by the reaction. U.S. Pat. No. 5,041,605 to Huson et al. discloses that some incorporated photographic amides can be prepared in the presence of water, and European Publication No. 0608896A1 to Sumitomo Chemical Co., Ltd. teaches that water alone can be used as an acid-absorbing reagent. In all cases, the acid chloride is added slowly to a solution of the amine in the presence of the acid-absorbing reagent to create a reaction mixture.

Since acid chlorides react very quickly with water, the success of preparations of incorporated photographic amides in the presence of water is unexpected. The absence of complete destruction of the acid chloride by the water is due to the nature of the groups on both the amine and acid chloride. That is, incorporated photographic amides must contain substituents that increase their solubility in water-insoluble solvents. Consequently, both the amine and the acid chloride are highly insoluble in water, promoting the desired reaction in the organic phase, and limiting the undesired hydrolysis of the acid chloride.

In typical batch operations to prepare incorporated photographic amides, concentrations of the amine and acid chloride to be combined are not always precisely known since solvent-wet starting materials are sometimes used to prepare these reagents. This lack of control results in multiple test-and-adjust cycles for each batch of amide. Moreover, in batch operations a large vessel is needed to contain the entire contents of the reaction mixture. In addition, much of the total processing time in batch mode is used for activities not related to the reaction. In particular, much time is allocated to steps such as reactor purging, reactant and solvent loading, heating, cooling, washing processing solutions free of salts, filtering the product solution prior to crystallization, and crystallizing and discharging the product.

All of these factors lead to high manufacturing cost due to the inefficient processing afforded by batch operations. As such, it would be desirable to reduce manufacturing cost by minimizing inefficiencies, thereby resulting in faster overall processing.

SUMMARY OF THE INVENTION

The present invention relates to a method of making an incorporated photographic amide comprising a) continuously combining an amine capable of forming an incorporated photographic amide, an acid chloride compound, one or more acid-absorbing reagents, and one or more water-immiscible solvents to continuously form a reaction mixture; b) continuously reacting the amine and acid chloride to form an incorporated photographic amide; and c) separating the incorporated photographic amide from the reaction mixture.

In another embodiment, the present invention relates to a method of making an incorporated photographic amide comprising a) continuously combining a quantity of an amine, a quantity of an acid chloride compound, a quantity of one or more acid-absorbing reagents, and a quantity of one or more water-immiscible solvents to form a reaction mixture; b) controlling the pH of the reaction mixture from 4 to 8; c) continuously reacting the amine and acid chloride to form an incorporated photographic amide; and d) separating the incorporated photographic amide from the reaction mixture, wherein the steps b) and c) may occur in any order including simultaneously.

Advantages of the invention will be obvious from the description, or may be learned by practice of the invention. Additional advantages of the invention will be realized and attained by means of the elements and combinations particularly pointed out in the appended claims. It is to be understood that both the foregoing general description and the following detailed description are exemplary and explanatory of preferred embodiments of the invention, and are not restrictive of the invention, as claimed.

DETAILED DESCRIPTION OF THE INVENTION

Figure 1:
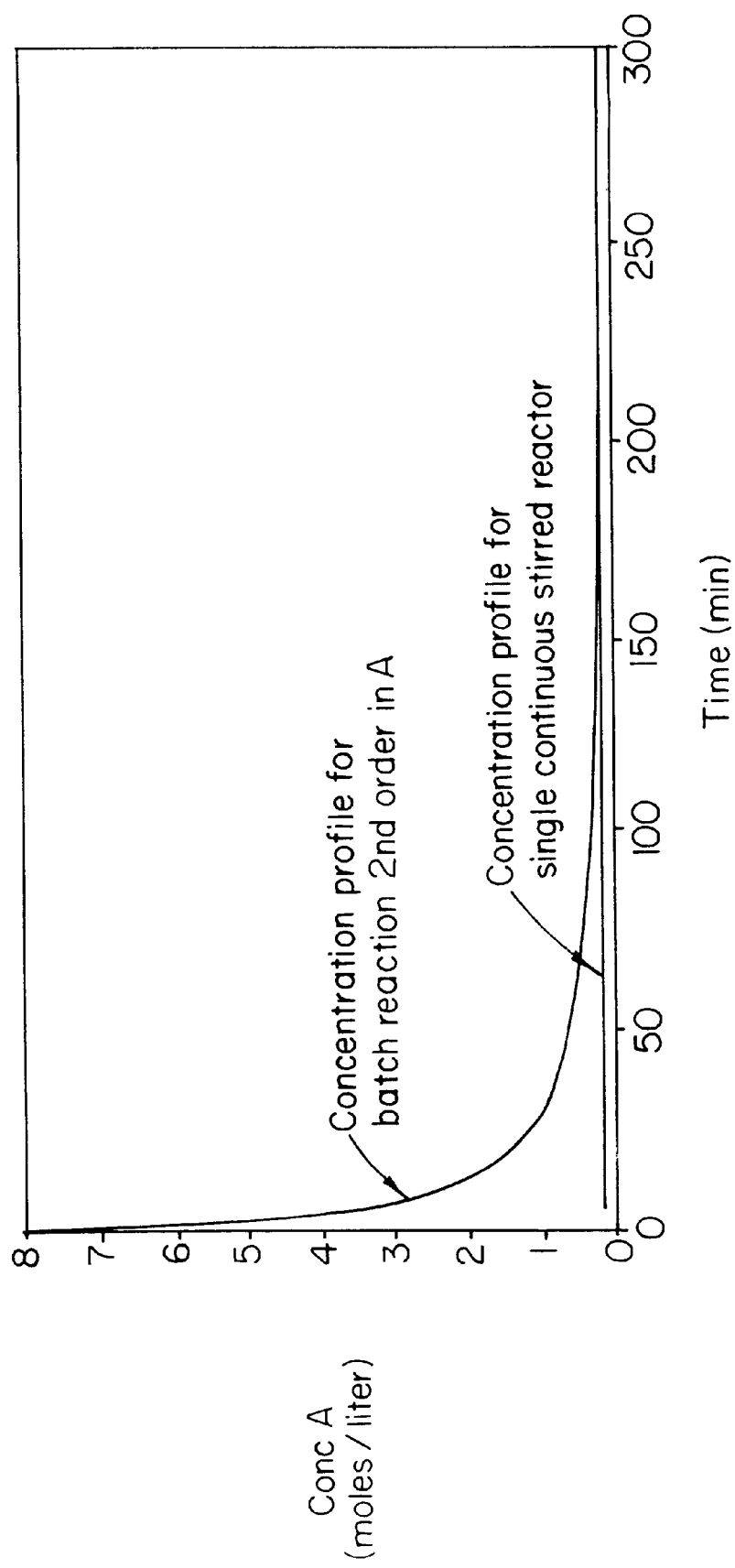
FIG. 1 is a graphical presentation of the expected concentration of amine when a process for producing an incorporated photographic amide is run in a batch mode.

The present invention may be understood more readily by reference to the following detailed description of the invention, including the Examples provided herein and the Figures. It is to be understood that this invention is not limited to the specific processes and conditions described, as specific processes and/or process conditions for producing photgraphic amides as such may, of course, vary. It is also to be understood that the terminology used herein is for the purpose of describing particular embodiments only and is not intended to be limiting.

It must also be noted that, as used in the specification and the appended claims, the singular forms "a," "an" and "the" comprise plural referents unless the context clearly dictates otherwise. For example, reference to processing or using a "composition" or "solvent" from the process of this invention is intended to comprise the processing of a plurality of compositions or solvents, potentially in a plurality of discrete processing steps.

Ranges may be expressed herein as from "about" or "approximately" one particular value and/or to "about" or "approximately" another particular value. When such a range is expressed, another embodiment comprises from the one particular value and/or to the other particular value. Similarly, when values are expressed as approximations, by use of the antecedent "about," it will be understood that the particular value forms another embodiment.

A weight percent of a component, unless specifically stated to the contrary, is based on the total weight of the formulation or composition in which the component is included.

By "continuously" it is meant that the process is substantially or completely continuous in operation and is to be contrasted with a "batch" process. "Continuously" is not meant in any way to prohibit normal interruptions in the contiuity of the process due to, for example, start-up, reactor maintenance, or scheduled shut down periods.

In one embodiment, the present invention relates to a method of making an incorporated photographic amide comprising a) continuously combining an amine capable of forming an incorporated photographic amide, an acid chloride, one or more acid-absorbing reagents, and one or more water-immiscible solvents to continuously form a reaction mixture; b) continuously reacting the amine and acid chloride to form an incorporated photographic amide; and c) separating the incorporated photographic amide from the reaction mixture.

In another embodiment, the invention relates to a method of making an incorporated photographic amide comprising a) continuously combining a quantity of an amine, a quantity of an acid chloride, a quantity of one or more acid-absorbing reagents, and a quantity of one or more water-immiscible solvents to form a reaction mixture; b) controlling the pH of the reaction mixture from 4 to 8; c) continuously reacting the amine and acid chloride to form an incorporated photographic amide; and d) separating the incorporated photographic amide from the reaction mixture, wherein the steps b) and c) may occur in any order including simultaneously.

The present invention thus provides a continuous process for producing an incorporated photographic amide. This continuous process provides yields comparable to a batch process, typically above about 75%, and preferably above about 85% based on the quantity of amine used in the reaction. The present invention also provides in-process product assays (on a solvent-free basis) typically above about 85%, and preferably above about 90%, again comparable to a batch process, measured, for example, by HPLC on a solvent-free basis.

The amines of the present reaction serve as the nitrogen donor and the backbone of the produced incorporated photographic amides. Consequently, any suitable water-insoluble amine capable of making an incorporated photographic amide may be used in this invention including primary amines and secondary amines.

One preferred class of amines is aromatic primary amines. Most preferably, the amines of the present invention have the formula shown in structures I or II, wherein $R_1$ is selected from the group consisting of hydrogen; $C_1$–$C_{25}$ alkyl unsubstituted or substituted with one or more groups selected from $C_1$–$C_{25}$ alkyl, $C_1$–$C_{12}$ alkoxy, $C_1$–$C_{12}$ alkoxycarbonyl, $C_7$–$C_{12}$ aryloxycarbonyl, $C_1$–$C_{12}$ aminocarbonyl, aryl, aryloxy, and $C_5$–$C_7$ cycloalkyl; aryl; and $C_5$–$C_7$ cycloalkyl and $R_2$, $R_3$, $R_4$ and $R_5$ are each independently selected from the group consisting of $C_1$–$C_{25}$ alkyl; $C_1$–$C_{25}$ alkoxy; aryloxy; $C_1$–$C_{25}$ alkylthio; $C_1$–$C_{25}$ dialkylamino; diarylamino; halogen; and hydrogen.

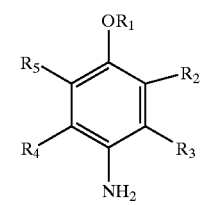

I

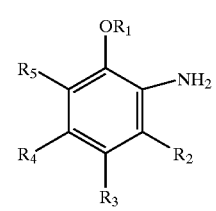

II

In a preferred embodiment, the amine is non-polar. Such amines are extremely soluble in an organic solvent phase and have limited water solubility. Examples of such water-insoluble amines include, but are not limited to, those of structures (a), (b), (c) and (d).

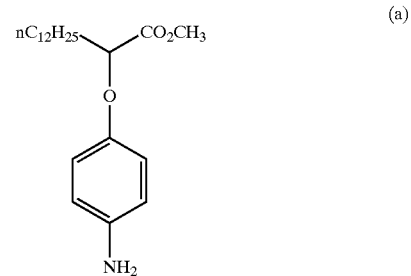

(a)

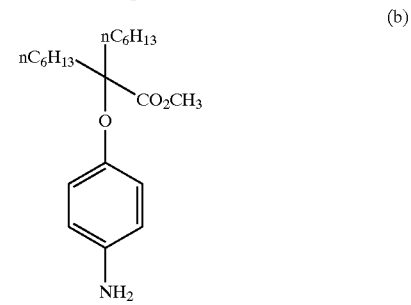

(b)

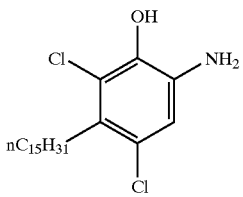
(c)

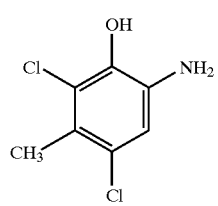
(d)

The amine(s) may be present in solution with a suitable solvent. To this end, the solvent must be water-immiscible, such as n-hexane, n-heptane, toluene, xylene, ethyl acetate, esters of $C_1$–$C_4$ carboxylic acids, or mixtures thereof. The solvent can also contain an alcohol such as methanol, ethanol, n-propanol, isopropanol, or n-butanol, or mixtures thereof, or mixtures of one or more alcohols with one or more water-immiscible solvents. Preferred alcohols include methanol and isopropanol. The concentration of the amine in such solvents is chosen to maximize reaction rates and give the desired concentration of the incorporated photographic amide. Typically, the concentration of the amine in the solvent is between about 10% and 80% (wt.), preferably between about 15% and 65% (wt.).

Any acid chloride capable of making an incorporated photographic amide is suitable for use in this invention. In a preferred embodiment, the acid chloride has limited water solubility and can be water insoluble. The acid chloride compound(s) of the present invention preferably include carboxylic and sulfonyl chlorides, such as $R_6COCl$ and $R_6SO_2Cl$ wherein $R_6$ is $C_1$–$C_{25}$ alkyl unsubstituted or substituted with one or more groups selected from $C_1$–$C_{25}$ alkyl, $C_1$–$C_{12}$ alkoxy, aryl, aryloxy, $C_5$–$C_7$ cycloalkyl; aryl; and $C_5$–$C_7$ cycloalkyl, each of which may be substituted or unsubstituted. Example acid chlorides include, but are not limited to, structures (e), (f), (g), and (h).

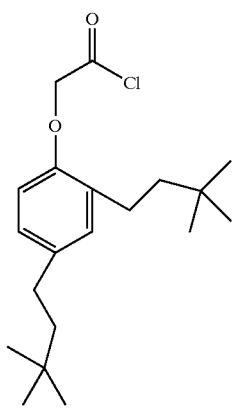
(e)

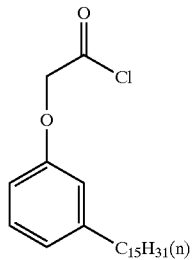
(f)

$C_{16}H_{22}SO_2Cl$ (g)

n-$C_9H_{19}COCl$ (h)

The acid chloride compound(s) may be added as a pure reagent, or dissolved in a water-immiscible solvent. Concentrations of acid chloride between about 20% and 100% (wt.) are typical, with concentrations of between about 50% and 100% (wt.) preferred. The acid chloride is added at a rate to allow a slight molar excess of acid chloride compared to the amine. Preferably, this molar excess is between about 1% and 25% more preferably between about 7% and 20%.

Further examples of amines and acid chlorides used to make the incorporated photographic amides and further examples of the resultant incorporated photographic amides include, but are not limited to, those disclosed in U.S. Pat. Nos. 2,875,057; 3,062,653; 5,561,037; and 5,009,989, which are herein incorporated by this reference in their entireties.

The acid-absorbing reagent serves to neutralize the hydrochloric acid liberated in the amide formation reaction. If the product does not contain acid-sensitive groups, such as in 2-[2,4-bis(1,1-dimethylpropyl)phenoxy]-N-[(3,5-dichloro-4-ethyl-2-hydroxyphenyl)]butanamide (1), then the acid-absorbing reagent may be comprised of substantially pure water. On the other hand, if the product contains an acid-sensitive group(s), such as in the ester group in Methyl 2-[4-[(butylsulfonyl)amino]phenoxy]tetradecanoate (2), then the acid-absorbing reagent may, in addition to water, contain a base capable of neutralizing the acid liberated by the reaction.

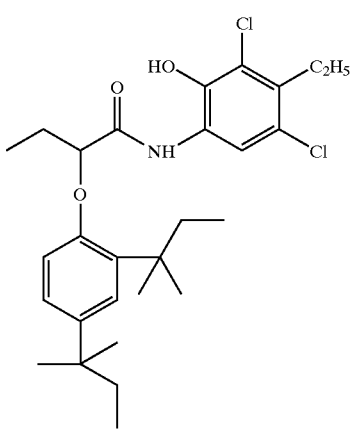
(1)

2-[2,4-bis(1,1-dimethylpropyl)phenoxy]-N-[(3,5-dichloro-4-ethyl-2-hydroxyphenyl)]butanamide (2)

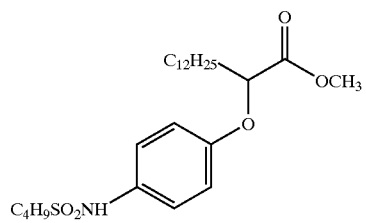

Methyl 2-[4-[(butylsulfonyl)amino]phenoxy]tetradecanoate

Any appropriate base may be chosen as an acid-absorber, but preferred bases include alkali metal hydroxides, bicarbonates, carbonates, carboxylates, and phosphates. Moreover, the acid-absorbing reagent may itself contain one or more organic bases, such as pyridine. The concentration of the base in the acid-absorbing reagent may be adjusted to control the pH of the reaction mixture in the reactor preferably between about 4 and about 8, more preferably between about 5 and about 7. The acid-absorber is typically water-containing The acid-absorbing reagent may be fed at a rate to maintain the water in the reactor at preferably from about 15% to 80% (wt.), more preferably from about 25% to 65% (wt.). The rate of the addition of the acid-absorbing reagent should be adjusted to provide efficient removal of acidic by-products.

The present invention includes at least one water-immiscible solvent. The water-immiscible solvent is included for ease of processing the product amide. Suitable water-immiscible solvents include, but are not limited to, n-hexane, n-heptane, toluene, xylene, ethyl acetate, (or other esters of $C_1$–$C_4$ carboxylic acids), or mixtures thereof. More preferred water-immiscible solvents include n-hexane, n-heptane, toluene, xylene, or mixtures thereof.

These solvents can be introduced in the amine feed and/or the acid chloride feed, or in a separate feed, in an amount such that the product amide is easily dissolved at the reaction temperature. The amide concentration in the water-immiscible solvent is preferably from about 10% to 50% (wt.), more preferably from about 20% to 40% (wt.).

The temperature of the reaction system is chosen so that the rate of the desired reaction is fast enough to complete the reaction in the desired amount of time. Generally, this temperature is from about 25° C. to 85° C., more preferably from about 40° C. to 80° C. The pressure is typically about one atmosphere. Preferably, the total residence time in the reaction system is from about 4 to 15 hours, more preferably from about 5 to 10 hours.

The solution of the incorporated photographic amide may be separated from the reaction mixture using any suitable means, including, but not limited to, batch and continuous separation processing. In one embodiment, the solution of the incorporated photographic amide is separated in batch mode by separating the water-immiscible layer in a Processing Tank, washing that layer with an aqueous solution, crystallizing the incorporated photographic amide by cooling the water-immiscible layer and filtering the resulting incorporated photographic amide crystals. All of these separation steps may also be done in a continuous manner by technology known to those of skill in the art.

The disclosed continuous process leads to improved process efficiency and reduced manufacturing cost. For instance, conventional batch preparation of an incorporated photographic coupler in a production reactor typically requires 30–45 hours total reactor time, consisting mainly of the following steps: loading of chemicals, heating and reaction time; washing of salts and impurities, cooling, crystallization, and filtration. In a 2000 gallon reactor, for example, a typical product yield could be 3400 lbs, giving a corresponding reactor production rate of 0.0375–0.0575 lbs/reactor gallon-hr.

The continuous production of an incorporated photographic coupler as described in the Examples herein would preferably include 2 reactors, each providing about 2–4 hours of residence time for the reaction mixture. The washing and crystallizing steps could be done continuously in less expensive equipment designed specifically for these purposes. Using the continuous process, two (2) 2000 gallon reactors could produce 375–750 gallons/hr of the total reaction mixture, which corresponds to 700–1500 lbs/hr of product (according to the ratios and concentrations described in Example 2). This provides a reactor production rate of 0.175–0.375 lbs/reactor gallon-hr—approximately 3–10 times the reactor production rate of the batch process.

Thus, by the process of the present invention, it has unexpectedly been found that a continuous process provides acceptable purity and yield, but with a much higher throughput rate than a batch process.

The success of the continuous preparation of the product amide is unexpected. FIG. 1 displays a typical second order concentration curve for compound A (the amine) in the presence of 1 equivalent of reactant B (the acid chloride). In continuous mode the steady-state concentration of amine at 98% conversion would be about 0.2 moles/liter, which is much lower than the average concentration of the amine in batch mode. Similarly, the steady state concentration of the product is much higher than its average concentration in the batch process. Therefore, competitive reactions such as acid chloride hydrolysis or reaction of the acid chloride with the product would have been expected to be more likely in the continuous process, and would have been expected to make the continuous processing economically unattractive. The examples provided show unexpectedly that competing reactions do not influence the yield and quality of the product when the reaction is run in continuous mode.

Figure 2:
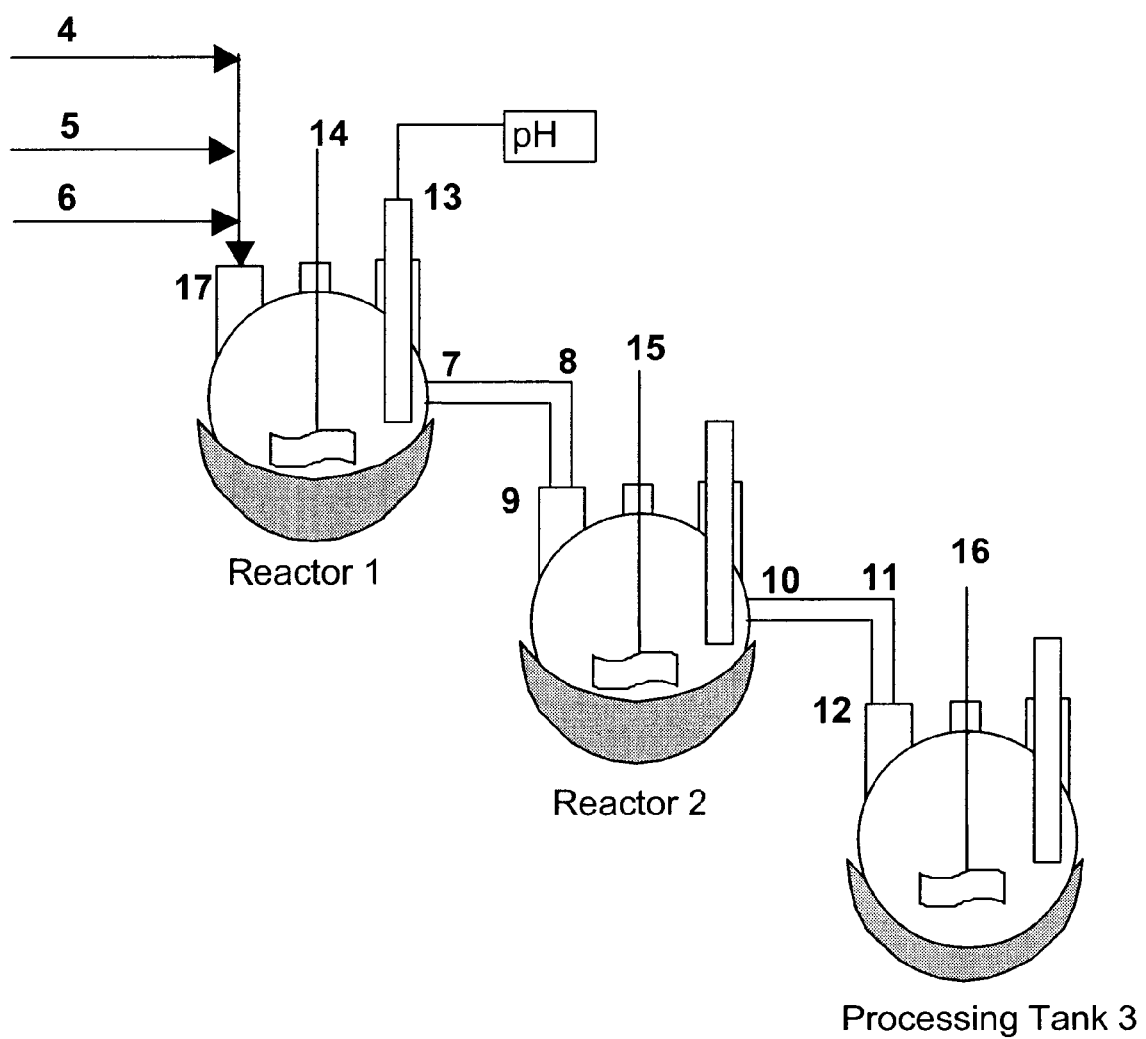
FIG. 2 is a process diagram of a preferred embodiment of the invention.

Referring now to FIG. 2, a preferred embodiment of the present invention which includes a reaction system having a first reactor (Reactor 1), a second reactor (Reactor 2) and a Processing Tank 3 in series. The Processing Tank 3 is used for washing the product free of salts and acid and for crystallizing the product. Reactor 1 and Reactor 2 and the Processing Tank 3 may be constructed of any materials compatible with the reaction and may be configured into any suitable shape. In practice, any number of reactors may be employed. If only one reactor is used, Reactor 1 acts as both Reactor 1 and Reactor 2 as described herein. Similarly, if more than two reactors are used, the reaction is carried forward to the additional reactors before entering the Processing Tank 3. The Processing Tank 3 can also be replaced by continuous extractors and continuous crystallizing equipment.

The amine, acid chloride, acid-absorbing reagent, and water-immiscible solvent starting materials are fed to Reactor 1 through inlet feed lines 4, 5, and 6, respectively, via inlet 17. Each of these starting materials may be metered into Reactor 1 via any appropriate means including positive displacement pumps to control the addition rate. Reactor 1 has an overflow outlet 7 near the top of the reactor. The overflow from Reactor 1 proceeds through outlet 7, through line 8 to the inlet 9 of Reactor 2. Similarly, Reactor 2 has an overflow outlet 10 near the top of the reactor. The Reactor 2 contents then flow through line 11 to the inlet 12 of Processing Tank 3.

Either Reactor 1 or Reactor 2, or both Reactors may have a pH monitoring system 13 that may include a pH probe and meter for monitoring the pH of the reaction. This pH monitoring system may be used to automatically add more starting material, such as the acid chloride compound or acid-absorbing reagent(s) when the pH of the reaction mixture goes outside of the desired range, which is preferably a range of from 4 to 8. In addition, each Reactor and the Processing Tank may have an agitator 14, 15, and 16, respectively, for mixing the reaction mixture.

Each reactor and the Processing Tank may have its own temperature and pressure control equipment including heaters, condensers, thermocouples, and nitrogen feeds. Any suitable temperature and pressure control equipment may be used and is dependent, at least in part, on the volume of the reaction mixture. For example, a Camile 1000® system (available from Argonaut Technologies Systems, Inc. of Indianapolis, Ind.), in conjunction with heating mantles, may be used to control temperatures.

The starting materials form a two phase system consisting of a water layer and water immiscible layer in Reactor 1. The reaction proceeds in the reactor system, and the product incorporated photographic amide resides in the water immiscible layer, which is the upper layer of the two phase system. The water immiscible layer may also contain at least some of the starting materials and any by-products of the reaction. The two phase system rises to the overflow outlet 7 as the volume increases, and thereby transfers to Reactor 2 via line 8 and inlet 9.

Similarly, the reaction continues in the Reactor 2 until the volume increases and to the overflow outlet 10, whereupon the reaction mixture transfers to the Processing Tank 3 via line 11 and inlet 12. The product incorporated photographic amide then undergoes physical processing steps in the Processing Tank 3, such as washing with water, and crystallization, and subsequent filtration.

EXPERIMENTAL

The following examples are put forth so as to provide those of ordinary skill in the art with a complete disclosure and description of how the compounds, compositions, and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in °C. or is at ambient temperature, and pressure is at or near atmospheric.

Comparative Example 1

Batch Mode Preparation of Methyl 2-[4-[(butylsulfonyl)amino]phenoxy]tetradecanoate (2)

A phosphate buffer solution composed of 49 g of water, 66 g of 45% aqueous potassium hydroxide (0.53 moles) and 38 g (0.32 moles) of 85% phosphoric acid was treated at room temperature with a solution of 69 g (0.197 moles) of methyl 2-[4-aminophenoxy]tetradecanoate (the amine) in 172 g of heptane. The temperature was adjusted to 30° C. and 37.1 g (0.237 moles) of butanesulfonyl chloride was added dropwise over 1 hr. The two-phase mixture was stirred for 4 hr while the temperature was maintained at 30° C. to 35° C. The product assayed 96.9% on a solvent-free basis. The bottom water layer was removed, and the upper layer was washed several times with 100 mL of water and was crystallized by cooling to ice temperature. The product was filtered and washed with 200 mL of cold heptane to afford 85 g (90% yield) of white solid, 98.9% assay by HPLC.

EXAMPLE 1

Continuous Preparation of Methyl 2-[4-[(butylsulfonyl)amino]phenoxy]tetradecanoate (2)

A heel was created batchwise by charging 142.2 g (0.41 moles) of methyl 2-[4-aminophenoxy]tetradecanoate (the amine), 267.7 g of heptane, 45.7 g (0.46 moles) of potassium bicarbonate, and 119.7 g of deionized water. The two-phase mixture was stirred with high agitation (800–900 rpm) and heated to 55° C–60° C. at which point 71.4 g of butanesulfonyl chloride was added over approximately 1 hour. After stirring for one hour, the composition of the assay of the product in the upper organic phase was 98.9%. At this point, continuous feeds into the reactor system, which consists of two reactors and a processing tank, were started to provide six hours of residence time in the two reactors. The feed rates were: 1.46 g/min (2.63 mmoles/min) of the amine solution (63 wt % in heptane), 0.45 g/min (2.87 mmoles/min) of the butanesulfonyl chloride, and 1.42 g/min (2.87 mmoles/min) of a 20 wt % potassium bicarbonate solution.

Figure 3:
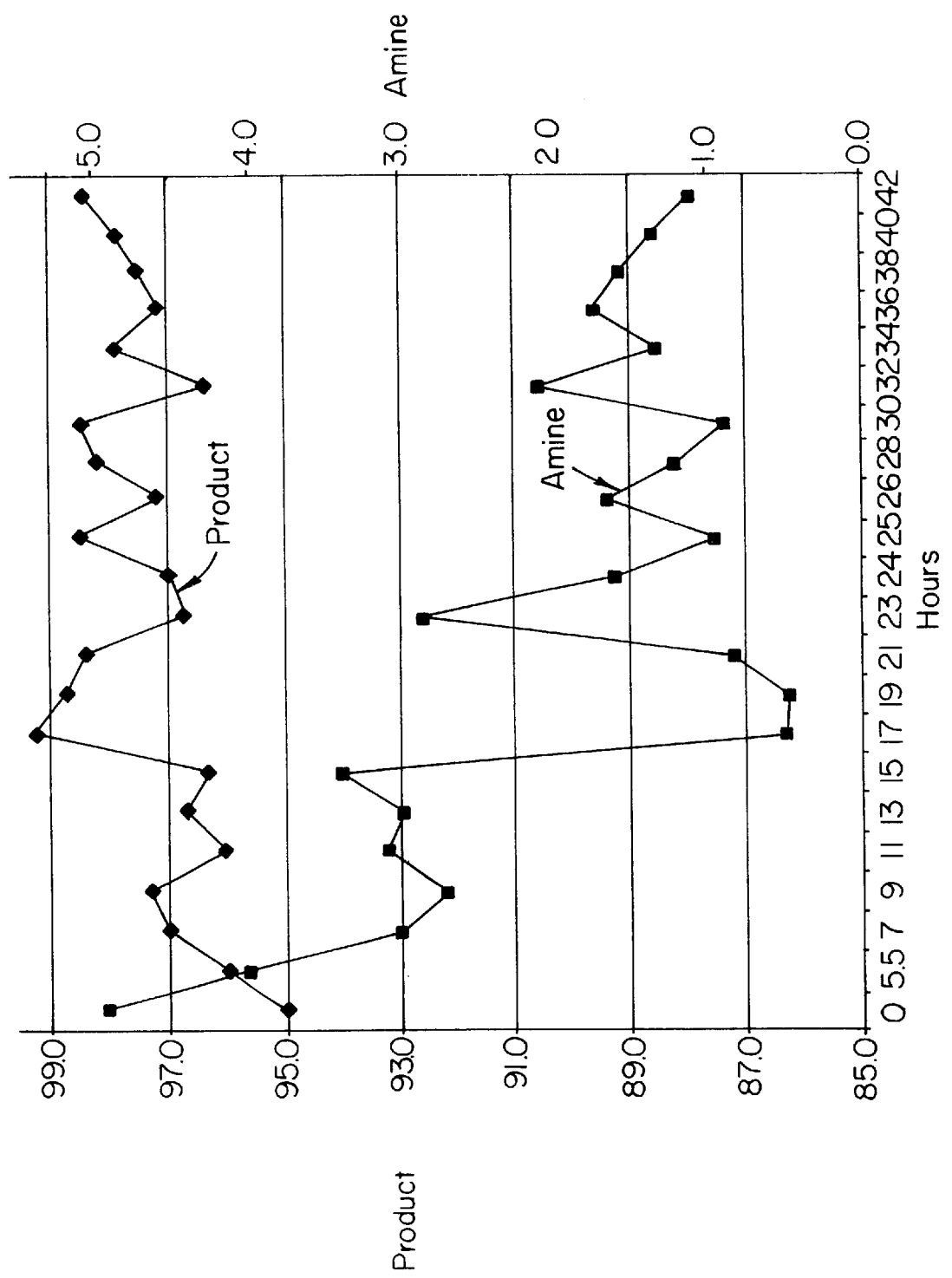
FIG. 3 is a graphical presentation of the results described in Example 1.

The results of the run are displayed in FIG. 3, which illustrates HPLC assays (on a solvent-free basis) of the % by weight over a 40 hour period for the amine and product amide. The assays are typical of assays obtained by batch operation (see Comparative Example 1). A 168 g sample exiting the reactor was washed free of residual salts and isolated as in Comparative Example 1 to give material of 98.1% assay in >95% yield.

Comparative Example 2

Batch Mode Preparation of 2-[2,4-bis(1,1-dimethylpropyl)phenoxy]-N-[(3,5-dichloro-4-ethyl-2-hydroxyphenyl)]Butanamide (1)

To a 4-neck flask with a gas inlet, condenser, thermometer, and addition funnel, 50 mL of deionized water and 31 g of sodium acetate was added and stirring was continued until the solid dissolved. At this point, 57 g of heptane, 20 g of toluene, and 30 g (0.146 moles) of 3,5-dichloro-4-ethyl-2-hydroxyaniline was added and the 2-phase mixture was warmed to 60° C. A solution of 53.2 g of 2-[2,4-bis(1,1-dimethylpropyl)phenoxy]butyryl chloride (0.157 moles, 8% excess) in 53 g of heptane was then added at 60° C.–65° C. The reaction was held for 2 hr at 60° C.–65° C., upon which time the area percent product by HPLC was 92% on a solvent-free basis. The two-phase mixture was heated to 75° C.–80° C. and held for 15 minutes. The agitator was stopped and the lower layer was decanted. The product solution was washed twice with 42 g of deionized water, cooled to 70° C. and seeded. The product slurry was cooled to 0° C.–5° C., and the product was collected by filtration, washed with cold heptane, and dried to give 66.9 g (90% yield), with an assay of 99.5% (wt.).

EXAMPLE 2

Continuous Preparation of 2-[2,4-bis(1,1-dimethylpropyl)phenoxy]-N-[(3,5-dichloro-4-ethyl-2-hydroxyphenyl)]Butanamide (1), With pH Control A heel was created via batch mode in Reactor 1 by first adding of 16 g (0.16 moles) of potassium bicarbonate, and 55 g of deionized water, and stirring until all of the solid had dissolved. Then, 24 g of isopropanol, 30 g (0.146 moles) of 3,5-dichloro-4-ethyl-2-hydroxyaniline (the amine), 120 g of heptane, and 20 g of toluene were added. The contents of the reactor system were heated to approximately 60° C. while agitating at 400 rpm. To this 2-phase mixture, 57.5 g (0.169 moles) of 2-[2,4-bis(1,1-dimethylpropyl)phenoxy]butyryl chloride (the acid chloride) were added over approximately 45 minutes. The analysis of the upper phase of the mixture was 94% product on a solvent free-basis. The continuous feeds were started at the following rates to provide six hours of residence time: 0.51 g/min 1.36 mmoles/min) of a 55 wt % solution of amine in isopropanol; 1.82 g/min (1.48 mmoles/min) of a solution of the acid chloride solution (27.5 wt % in a mixture of 6 parts of heptane and 1 part of toluene. A 22.5 wt % solution of potassium bicarbonate in water was added to maintain the pH between about 2 and 4. The flowrate of the potassium bicarbonate solution ranged from 0.64–0.68 g/min (1.37–1.46 mmoles/minute).

Figure 4:
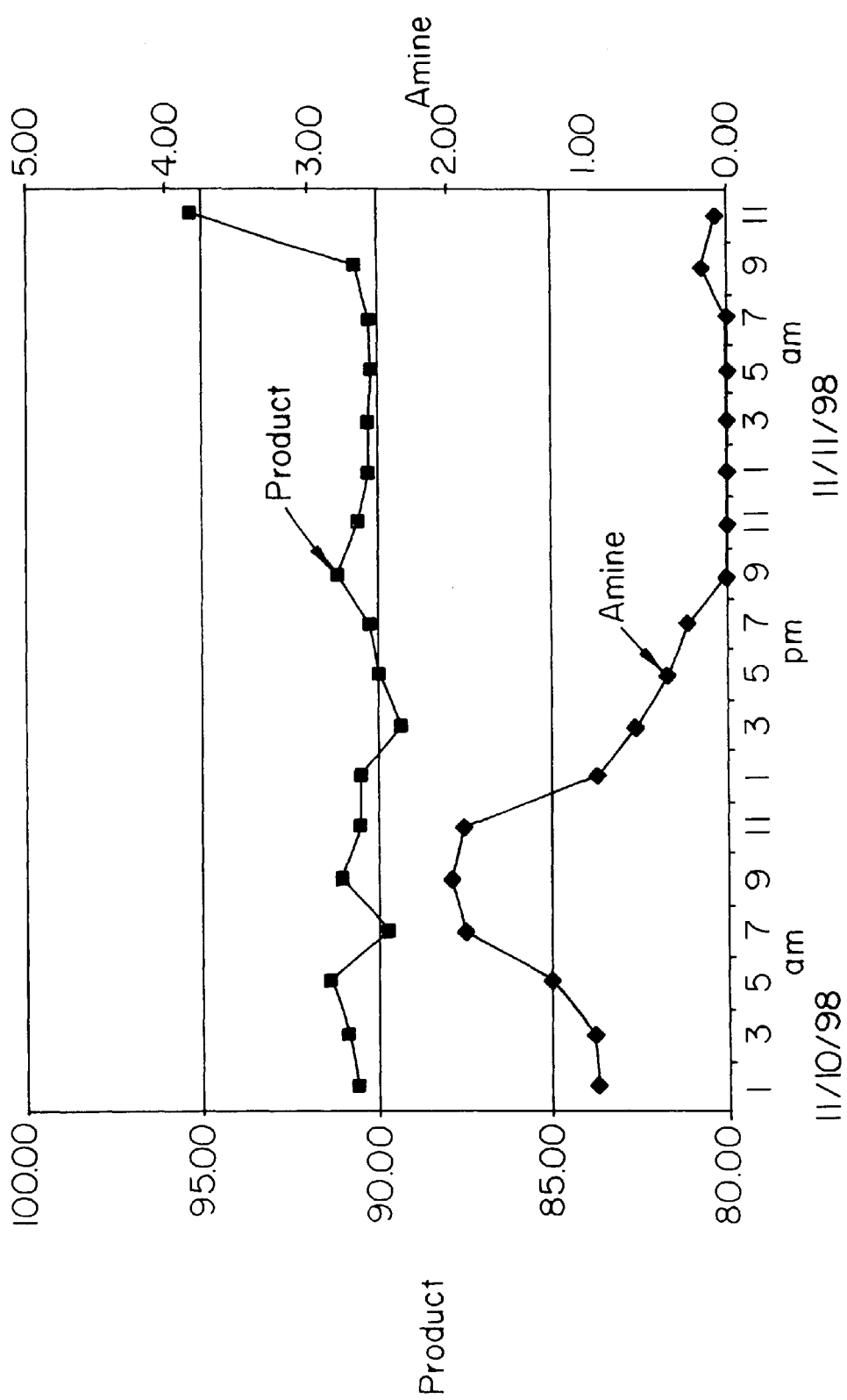
FIG. 4 is a graphical presentation of the results described in Example 2.

The results of the run are displayed in FIG. 4, which illustrates HPLC assays (on a solvent-free basis) of the % by weight over a 32 hour period for the amine and product amide. The assays are typical of assays obtained by batch operation (see Comparative Example 2). A 250 g sample exiting the reactor was washed free of residual salts and isolated as in Comparative Example 2 to give material of 99.7% assay in 92% yield.

EXAMPLE 3

Continuous Preparation of 2-[2,4-bis(1,1-dimethylpropyl)phenoxy]-N-[(3,5-dichloro-4-ethyl-2-hydroxyphenyl)]Butanamide, Without pH Control A heel was created via batch mode by first adding of 16 g (0.16 moles) of potassium bicarbonate, and 55 g of deionized water, and stirring until all of the solid had dissolved. Then 24 g of isopropanol, 30 g (0.146 moles) of 3,5-dichloro-4-ethyl-2-hydroxyaniline (the amine), 120 g of heptane, and 20 g of toluene were then added. The contents of the reactor system were heated to approximately 60° C. while agitating at 400 rpm. To this 2-phase mixture 57.5 g (0.169 moles) of 2-[2,4-bis(1,1-dimethylpropyl)phenoxy] butyryl chloride (the acid chloride) were added over approximately 45 minutes. The analysis of the upper phase of the mixture was 91.8% on a solvent-free basis. The reaction temperature was raised to reflux. (68° C.–75° C.), and the continuous feeds were started at the following rates to provide six hours of residence time: 0.67 g/min of water; 0.51 g/min (1.36 mmoles/min) of a 55.5% (wt.) solution of the amine in isopropanol; and 1.82 g/min (1.48 mmoles/min)of a solution of the acid chloride solution 27.5% (wt.) in a mixture of 6 parts of heptane and 1 part of toluene. The water phase became highly acidic since the pH was not controlled in this run.

Figure 5:
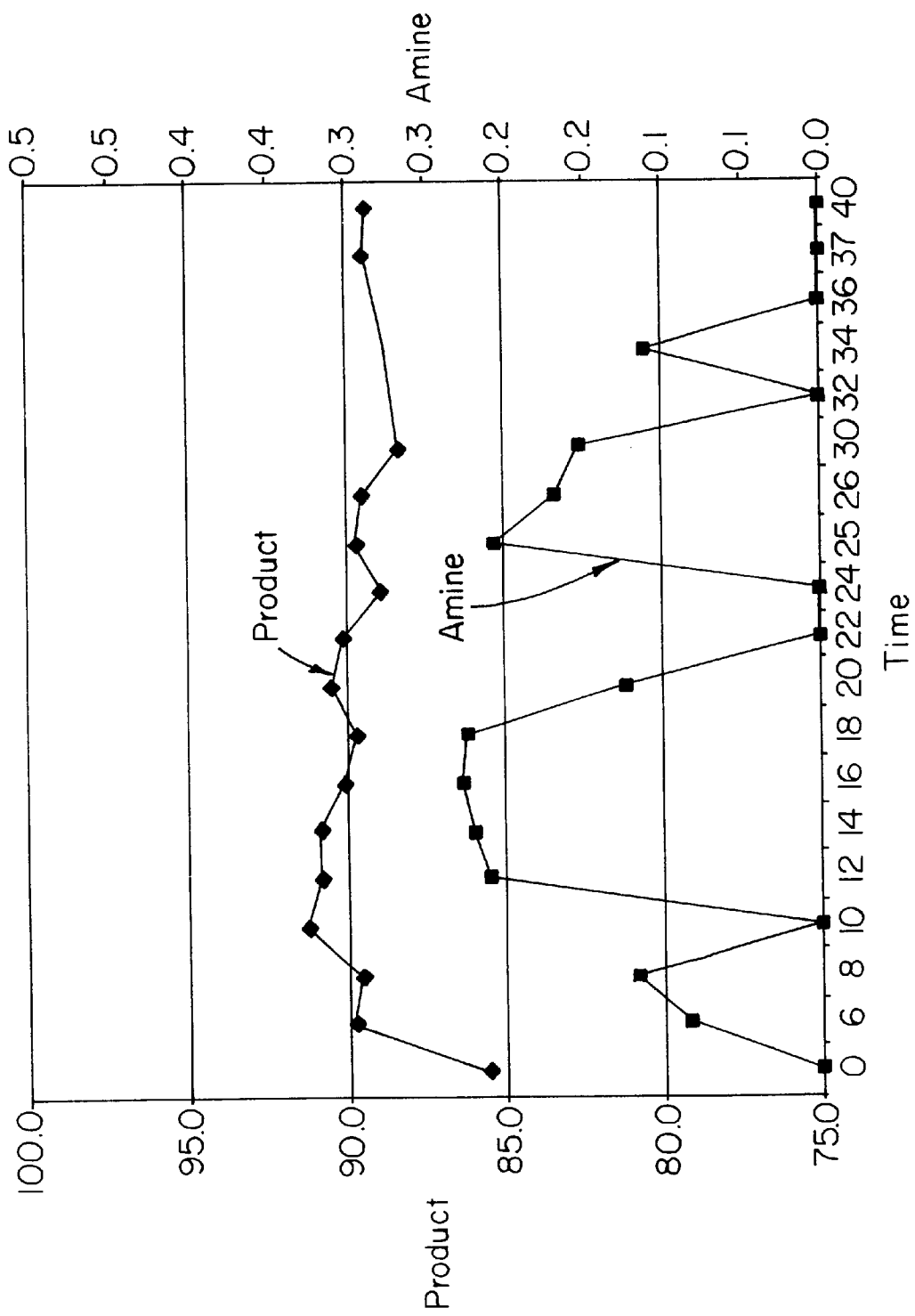
FIG. 5 is a graphical presentation of the results described in Example 3.

The results of the run are displayed in FIG. 5, which illustrates HPLC assays (on a solvent-free basis) of the % by weight over a 40 hour period for the amine and product amide. The in-process and isolated product assays as well as the isolated yield, are typical of those obtained by batch operation (see Comparative Example 2).

Throughout this application, various publications are referenced. The disclosures of these publications in their entireties are hereby incorporated by reference into this application in order to more fully describe the state of the art to which this invention pertains.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method of making an incorporated photographic amide comprising:
   a) continuously combining, at a temperature of 25° C. to 85° C., an amine according to formula I or II,

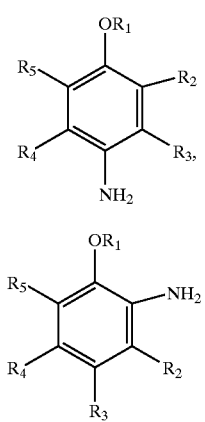

or mixtures thereof, an acid chloride according to $R_6SO_2Cl$, $R_6COCl$, or mixtures thereof, one or more water containing acid-absorbing reagents, and one or more water-immiscible solvents to continuously form a reaction mixture;
   b) continuously reacting the amine and acid chloride to form an incorporated photographic amide; and
   c) separating the incorporated photographic amide from the reaction mixture, wherein $R_1$ is hydrogen; $C_1$–$C_{25}$ alkyl unsubstituted or substituted with one or more groups of $C_1$–$C_{25}$ alkyl, $C_1$–$C_{12}$ alkoxy, $C_1$–$C_{12}$ alkoxycarbonyl, $C_7$–$C_{12}$ aryloxycarbonyl, $C_1$–$C_{12}$ aminocarbonyl, aryl, aryloxy, and $C_5$–$C_7$ cycloalkyl; aryl; or $C_5$–$C_7$ cycloalkyl; $R_2$, $R_3$, $R_4$ and $R_5$, independently are $C_1$–$C_{25}$ alkyl; $C_1$–$C_{25}$ alkoxy; aryloxy; $C_1$–$C_{25}$ alkylthio; $C_1$–$C_{25}$ dialkylamino; diarylamino; halogen, and hydrogen; and $R_6$ is $C_1$–$C_{25}$ alkyl unsubstituted or substituted with one or more groups of $C_1$–$C_{12}$ alkoxy, aryl, aryloxy, and $C_5$–$C_7$ cycloalkyl; aryl; and $C_5$–$C_7$ cycloalkyl.

2. A method according to claim 1 wherein the pH of the reaction mixture is maintained at a range of from about 4 to about 8.

3. The method of claim 2, wherein the acid-absorbing reagent comprises at least one alkali metal hydroxide, bicarbonate, carbonate, carboxylate, phosphate, or a mixture thereof; and the water-immiscible solvent comprises n-hexane, n-heptane, toluene, xylene, ethyl acetate, an ester of a $C_1$–$C_4$ carboxylic acid, or a mixture thereof.

4. The method of claim 3, wherein the incorporated photographic amide comprises methyl 2-[4-[(butylsulfonyl)amino]phenoxy]tetradecanoate or 2-[2,4-bis(1,1-dimethylpropyl)phenoxy]-N-[(3,5-dichloro-4-ethyl-2-hydroxyphenyl)]Butanamide.

5. The method of claim 1, wherein the amine is in solution with a water immiscible solvent, an alcohol, or a mixture thereof.

6. The method of claim 1, wherein the acid-absorbing reagent comprises water.

7. The method of claim 1, wherein the water-immiscible solvent comprises n-hexane, n-heptane, toluene, xylene, ethyl acetate, an ester of a $C_1$–$C_4$ carboxylic acid, or a mixture thereof.

* * * * *